US005571504A

United States Patent [19]

Nakayama et al.

[11] Patent Number: 5,571,504

[45] Date of Patent: Nov. 5, 1996

[54] METHOD OF STABILIZING PREPARATIONS FOR CONTACT LENSES

[75] Inventors: Hisayuki Nakayama, Akashi; Akihiro Kimoto, Kobe; Kuniko Tsuchino, Osaka, all of Japan

[73] Assignee: Senju Pharmaceutical Co., Ltd., Osaka, Japan

[21] Appl. No.: 317,660

[22] Filed: Oct. 3, 1994

[30] Foreign Application Priority Data

| | | | |
|---|---|---|---|
| Oct. 1, 1993 | [JP] | Japan | 5-270045 |
| Aug. 11, 1994 | [JP] | Japan | 6-211834 |

[51] Int. Cl.[6] .......... A61K 33/18

[52] U.S. Cl. .......... 424/78.04; 514/423; 514/839; 514/840; 422/28

[58] Field of Search .......... 514/423, 839, 514/840; 424/78.04

[56] References Cited

U.S. PATENT DOCUMENTS

| | | | |
|---|---|---|---|
| 4,863,952 | 9/1989 | Abe et al. | 514/423 |
| 4,976,969 | 12/1990 | Plamondon | 514/840 |
| 5,171,526 | 12/1992 | Wong et al. | 514/840 |
| 5,322,667 | 6/1994 | Sherwood | 514/840 |
| 5,352,695 | 10/1994 | N'Guyen et al. | 514/423 |
| 5,411,598 | 5/1995 | Tsao et al. | 514/840 |

FOREIGN PATENT DOCUMENTS

| | | | |
|---|---|---|---|
| 4038692 | 6/1992 | Germany | 424/76.04 |
| WO91/07192 | 5/1991 | WIPO | 427/76.04 |

OTHER PUBLICATIONS

JP-A-5179291, *Derwent Publications Ltd.*, Jul. 20, 1993.
Copy of European Search Report dated Feb. 21, 1996.

*Primary Examiner*—James H. Reamer
*Attorney, Agent, or Firm*—Merchant, Gould, Smith, Edell, Welter & Schmidt, P.A.

[57] ABSTRACT

With a specific aim to preventing the proteolytic enzyme in a preparation for contact lenses containing a proteolytic enzyme from deterioration in the state of aqueous solution, the present invention provides (1) a method of stabilizing a preparation for contact lenses containing a proteolytic enzyme, which comprises formulating the said preparation with a pyrrolidone compound, (2) a process for producing a prepration for contact lenses and (3) a preparation for contact lenses.

The preparation according to the present invention can be processed into the liquid or solid preparation form, wherein the liquid preparation can be processed into a one-component type preparation. The liquid preparation as well as the solid preparation, even after being dissolved in water, can maintain the activity of the proteolytic enzyme over a prolonged period of time, and can be used effectively for cleansing and cleaning, preservation and sterilization of contact lenses.

14 Claims, No Drawings

METHOD OF STABILIZING PREPARATIONS FOR CONTACT LENSES

This invention relates to a novel and useful method of stabilizing proteolytic enzymes. In more particular, the present invention is concerned with a method of stabilizing preparations for contact lenses containing proteolytic enzymes, which method comprises adding a pyrrolidone compound to the preparations.

Contact lenses are roughly classified into two types, or hard and soft contact lenses. Although the hard contact lenses, with their non-hydrophilic property, are said to show reduced oxygen permeability, the hard contact lenses with improved oxygen permeability have recently been developed. However, both kinds of contact lenses are readily dirt-deposited with proteins, etc., and in addition, the oxygen-permeable lenses require the daily care by cleansing and cleaning, sterilization and preservation in order to keep their desired oxygen permeability in order.

Proteolytic enzymes are used to remove protein dirt adhered on the surface of contact lenses, and actually, there have been proposed and put in use a great variety of cleansing and cleaning preparations containing such proteolytic enzymes. For example, preparations composed mainly of proteolytic enzymes, which are supplied in the form of solids, such as tablets, granules and powders, are dissolved in purified water, etc. on the occasion of cleansing and cleaning of contact lenses by their wearers. Since such application procedure makes it necessary for wearers to dissolve in purified water, etc. the proteolytic enzyme in the solid form on every occasion of use, nevertheless, the wearers are forced to endure inconvenience from increased costs and troublesome procedures, while at the same time they are troubled with time-course reduction in enzymatic activity after dissolution. Such being the case, there have also been proposed methods of stabilizing a proteolytic enzyme in the state of solution; for example, the Japanese Unexamined Patent Publication Nos. 159822/1988 and 180515/1989 propose the method of stabilizing a proteolytic enzyme which comprises incorporating a proteolytic enzyme into a solution containing a water-miscible polyhydric alcohol. However, the resultant solution preparation as such hardly exhibits enzymatic activity, and it can be diluted with water to produce increased enzymatic activity, but suffers from the disadvantage of deteriorated stability.

The present invention has been completed in view of the above-described situations and is intended to stabilize a proteolytic enzyme in a solution to thereby provide a liquid preparation for contact lenses which, solely and without use of any auxiliaries, can permit contact lenses to be cleansed and cleaned, sterilized and preserved simultaneously.

The present inventors conducted repeatedly intensive investigation into the stability of proteolytic enzymes capable of removing protein dirt and as a result, found that addition of a pyrrolidone compound unexpectedly can lead to prolongation or extension of the stability of such proteolytic enzymes in a solution being designed for use in cleansing and cleaning contact lenses, without deteriorating their activities. This finding, followed by further continued research, has culminated into the present invention.

The present invention relates to a method of stabilizing a liquid preparation for contact lenses containing proteolytic enzymes which comprises adding a pyrrolidone compound to a solution containing an effective amount of a proteolytic enzyme, to liquid preparations for contact lenses containing a proteolytic enzyme which is stabilized by use of the said method and to a process for producing such liquid preparations.

The pyrrolidone compounds which are usable in the present invention may be any of 2-pyrrolidone, D-, L- or DL-pyrrolidonecarboxylic acid (namely, 2-pyrrolidone-5-carboxylic acid); or their salts, for example, sodium salts, potassium salts or amine salts, such as triethanolamine salts; or their esters, for example, ethyl esters, which compounds can suitably be utilized. The used amount of such pyrrolidone compounds can suitably be chosen depending upon the kind of pyrrolidone compounds, the type of contact lenses to be cleaned, the nature and extent of dirt deposits to be removed, etc. In the light of the fact that the presence of such pyrrolidone compound in the solution at a concentration of lower than 5 (W/V) % fails to provide satisfactory enzymatic stability, it is difficult to supply prospective users with such preparations in the solution state. Consequently, such pyrrolidone compounds are desirably used at a concentration of normally not less than 5 (W/V) %, preferably in the range of 10 to 60 (W/V) %.

The proteolytic enzymes which are useful in this invention include trypsin and chymotrypsin as well as proteases derived from microorganisms of the genera Bacillus and others. The formulation amount of such proteolytic enzymes is suitably determined based on the effective quantity sufficiently to achieve the intended cleansing and cleaning effect, and is decided to be employed at such a ratio as may correspond to the region of preferably 10 to 5,000 units/ml, more preferably 50 to 1,000 units/ml. This is simply because such proteolytic enzymes when formulated in too small amounts fail to produce the satisfactory cleansing and cleaning effect, while the enzymes used at too much increased concentrations incur the risk of causing damages to the skin during the cleansing and cleaning procedure.

The preparations for contact lenses, which are prepared according to the present invention, desirably are normally adjusted to a pH value in the range of 4 to 8 for the purpose of stabilization of the proteolytic enzymes employed.

According to the present invention, the preparations for contact lenses can take the form of either solid or liquid, and the form of preparation is not particularly limited only if it can be rendered into the state of solution on the occasion of use, and can be exemplified by the liquid preparation as well as the solid preparation which can be stored for a long period of time and is suited for use through dissolution on the occasion of use. In the case of the liquid preparation, especially, the solutions containing proteolytic-enzyme according to the present invention are extremely useful and advantageous in that the said solutions, when formulated with a pyrrolidone compound, not only develop enhanced enzymatic activity while they keep the proteolytic enzymes stable in the aqueous solution, but also eliminate the need for dilution with water on the occasion of use as is normally the case with the conventional stabilized enzyme solutions for contact lenses containing polyhydric alcohols such as glycerol. As the solid form of preparation, there may be mentioned tablets, granules, powders and lyophilizates, and the lyophilizates are preferred in that it dissolves fast, shows sterility and provides the composition with uniformity. The above-described amounts of the pyrrolidone compounds, surfactants and proteolytic enzymes to be formulated are expressed in terms of those being present in a solution-form preparation for contact lenses prepared from the solid form on the occasion of use.

In addition to the above described components, there can furthermore be formulated excipients, such as other surfactants, preservatives, pH regulating agents, buffers, chelating agents, disintegrating agents and binders, as well as different enzymes, such as lipases, and other various additives.

As the surfactants, nonionic, anionic and amphoteric surfactants are effective, and these surfactants can be used in combination, if desired.

The anionic surfactants include, for example, sodium lauroylsarcosine, triethanolamine lauroyl-L-glutamate and sodium myristylsarcosine, and examples of the amphoteric surfactants include lauryldimethylaminoacetic betaine, 2-alkyl-N-carboxymethyl-N-hydroxyethylimidazolinium betaine and alkyldiaminoglycine hydrochloride, while as the nonionic surfactants, there may be mentioned polysorbate 80, polyoxyethylenated hardened castor oil 60, polyoxyl 40 stearate and polyoxyethylene lauryl ether.

The amount of the surfactants to be formulated may arbitrarily be selected only if they can provide such a concentration as may achieve a satisfactory degree of enzymatic stability without causing any adverse effect on the contact lenses and ophthalmic tissues, and are employed in such a manner as may give their concentrations in the range of preferably 0.01 to 10 (W/V) %, more preferably 0.1 to 5 (W/V) %.

The preparations for contact lenses as stabilized according to the method of the present invention can be put into use by placing one piece of contact lens removed from the eyeball in 5 ml of the preparation for contact lenses in the liquid form (e.g., the preparation for contact lenses in the aqueous solution state), followed by immersion for a period of time of not less than 30 min. to thereby accomplish spontaneous cleansing and cleaning and sterilization simultaneously: the contact lens after being soaked is rinsed with tap water and worn on the cornea of the eye again. The field test conducted by the present inventors indicated that the preparations for contact lenses in the solution state, after consecutive daily use for one week, brought about no controversy or problem.

The present invention can thus permit the proteolytic enzyme in a preparation for contact lenses containing a proteolytic enzyme to be maintained stable in the liquid state. Consequently, the stabilized preparation for contact lenses containing a proteolytic enzyme according to this invention can achieve the simultaneous cleaning, sterilization and preservation of contact lenses, with one preparation solely and without use of any additional means, and can offer the advantage that it cans be used in the simple and convenient manner with improved processability, since dirt can be effectively removed from contact lenses simply through soaking and standing and that any further treatment procedure such as dilution with water is not required in the case of the solution preparation.

The experiment example and examples are described in the following to illustrate specifically the present invention, but it should be understood that these only serve a purpose to give the illustration of this invention and shall in no way limit its scope.

EXPERIMENT EXAMPLE 1

Test on the Removal of Protein Dirt

Two oxygen-permeable hard contact lenses (made of siloxanyl methacrylate) adhered with artificially prepared dirt based on lysozyme chloride, etc. were soaked in the cleansing and cleaning solutions for contact lenses having the composition as shown in Table 1 and containing individually 10% and 40% of sodium DL-pyrrolidonecarboxylate as a stabilizer and a cleansing and cleaning solution comprising 40% of glycerol, respectively, followed by standing for 15 hours. The contact lenses were washed with water and examined with the naked eye for removal and cleaning of the artificial dirt deposited thereon. The results are tabulated below, which leads to the confirmation that the cleaning solutions with 10% and 40% of a sodium DL-pyrrolidonecarboxylate content removed the artificial dirt completely, whereas the cleaning solution containing 40 % of glycerol did not eliminate the artificial dirt at all.

Results:

| Test solution | Before | After |
|---|---|---|
| 10% of sodium DL-pyrrolidonecarboxylate | +++ | – |
| 40% of sodium DL-pyrrolidonecarboxylate | +++ | – |
| 40% of glycerol | +++ | +++ |

Note:
+++: a white turbid state observed on the lens surface.
–: no dirt observed on the lens surface.

The contact lenses deposited with artificially prepared dirt were prepared by the following procedure:

The artificial dirt solution of the below-described formulation was prepared, degassed and heated at about 60° C., and the lenses were placed in the solution, taken out of it when they became turbid to an appropriate degree, and gotten rid of lumps of dirt, followed by storage in water.

| Substance | Amount |
|---|---|
| Lysozyme chloride | 0.1 g |
| Disodium hydrogenphosphate | 0.2 g |
| Sodium hydroxide | q.s. |
| Purified water | q.s. |
| Total | 100 ml (at pH 7.2) |

EXAMPLE 1

The formulation ingredients as described in Tables 1 and 2 were mixed for dissolution to thereby prepare different test solutions. The thus-prepared test solutions were subjected to assay of the enzymatic activities based on the Anson-Ogiwara's modified method immediately after being prepared and after being stored at a temperature of 30° C. for 7 and 14 days, respectively, followed by calculation of the residual rate of enzymatic activities (%) following the below-described equation, with the results being shown in Tables 1 and 2.

$$A\ (\%)=E/E_0\times 100$$

where:

A=Residual rate of enzymatic activity

E=Enzymatic activity after being stored at 30° C. for 7 or 14 days $E_0$=Enzymatic activity immediately after being prepared.

As is obvious from Tables 1 and 2, addition of the pyrrolidone compound to a solution containing a proteolytic enzyme was observed to result in marked stabilization of the proteolytic enzyme in the said solution.

EXAMPLE 2

The formulation ingredients as described in Table 3 were mixed for dissolution to thereby prepare a test solution, which was determined for the residual rate of enzymatic activity (%) in the same manner as mentioned in Example 1, with the results being shown in Table 3.

As is evident from the test results shown in the columns B-6 of Table 1 and B-8 of Table 3, incorporation of a pyrrolidone compound as well as anionic surfactants and a nonionic surfactant was found to bring about enhanced stabilization of the proteolytic enzyme.

EXAMPLE 3

| Substance | Amount |
|---|---|
| Bioprase | 1,500 units |
| Triethanolamine lauroyl-L-glutamate (30%) | 0.1 g |
| Alkyldiaminoglycine hydrochloride | 0.03 g |
| Sodium DL-pyrrolidonecarboxylate (50%) | 4.8 g |
| Boric acid | 0.03 g |
| Borax | 0.018 g |
| Sodium edetate | 0.006 g |
| Chlorhexidine gluconate | 0.3 mg |

The above-described formulation ingredients were dissolved in 6 ml of purified water to give a preparation for contact lenses containing the proteolytic enzyme, which was determined for the residual rate of enzymatic activity in the same manner as described in Example 1. The preparation, after being stored at 30° C. for 14 days, was found to retain not less than 95% of the enzymatic activity and produced good cleaning effect. In the lipid- and protein-removal tests, the preparation was found to give satisfactory results, with no substantial microbial growth being noted.

EXAMPLE 4

| Substance | Amount |
|---|---|
| Trypsin | 1,400 units |
| Polyoxyl 40 stearate | 0.03 g |
| 2-Pyrrolidone | 2.1 g |
| Chlorohexidine gluconate | 0.6 mg |
| Disodium hydrogenphosphate | 0.012 g |
| Phosphoric acid | q.s. |
| Sodium chloride | 0.051 g |

The above-described formulation ingredients were dissolved in 6 ml of purified water to produce a preparation for contact lenses containing a proteolytic enzyme. The resultant test solution was subjected to the same test as described in Example 3, with the similar, satisfactory results being obtained.

EXAMPLE 5

| Substance | Amount |
|---|---|
| Bioprase | 2,880 units |
| Triethanolamine lauroyl-L-glutamate (30%) | 0.2 g |
| Polyoxyl stearate 40 | 0.06 g |
| Lauryldimethylaminoacetate betaine (35%) | 0.17 g |
| Boric acid | 0.03 g |
| Sodium edetate | 0.006 g |
| Sodium DL-pyrrolidonecarboxylate (50%) | 3.6 g |

The above-described formulation ingredients were dissolved in 6 ml of purified water, followed by adjustment to pH 6.0 with hydrochloric acid to produce a preparation for contact lenses containing a proteolytic enzyme. The resultant test solution was subjected to the same test as described in Example 3, with the similar, satisfactory results being obtained.

EXAMPLE 6

| Substance | Amount |
|---|---|
| Bioprase | 2,800 units |
| Sodium lauroylsarcosinate | 0.06 g |
| Betaine lauryldimethylacetate (35%) | 0.17 g |
| Polyoxyethylene lauryl ether | 0.03 g |
| Ethyl DL-pyrrolidonecarboxylate | 1.5 g |
| Sorbic acid | 0.006 g |
| Boric acid | 0.06 g |
| Borax | q.s. |

The above-described formulation ingredients were dissolved in 6 ml of purified water, followed by adjustment to pH 6.0 with hydrochloric acid to produce a preparation for contact lenses containing a proteolytic enzyme. The resultant test solution was subjected to the same test as described in Example 3, with the similar, satisfactory results being obtained.

TABLE 1

| | Formulation | | | | | | | |
|---|---|---|---|---|---|---|---|---|
| Substance | Reference B | B-1 | B-2 | B-3 | B-4 | B-5 | B-6 | B-7 |
| Bioprase (unit/ml) | 240 | 240 | 240 | 240 | 240 | 240 | 240 | 240 |
| Disodium DL-pyrrolidonecarboxylate | — | 60.0% | 40.0% | 30.0% | 20.0% | 10.0% | 5.0% | 0.5% |
| Sodium hydrogenphosphate | 0.2% | 0.2% | 0.2% | 0.2% | 0.2% | 0.2% | 0.2% | 0.2% |
| Phosphoric acid | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. |
| Sodium chloride | 0.9% | 0.9% | 0.9% | 0.9% | 0.9% | 0.9% | 0.9% | 0.9% |
| Purified water | q.s. | q.s. | q.s. | q.s. | q.s. | q.s. | q.s. | q.s. |
| pH | 7.0 | 7.0 | 7.0 | 7.0 | 7.0 | 7.0 | 7.0 | 7.0 |
| Residual rate of enzymatic activity (%), at 30° C. for 7 days | 69.5 | 99.2 | 99.1 | 87.9 | 94.5 | 84.5 | 84.8 | 70.2 |
| Residual rate of enzymatic activity (%), at 30° C. for 14 days | 66.8 | 98.3 | 97.4 | 90.2 | 84.8 | 84.0 | 71.9 | 61.4 |

TABLE 2

| Substance | Formulation Reference T | T-1 | T-2 | T-3 | T-4 | T-5 |
|---|---|---|---|---|---|---|
| Trypsin (unit/ml) | 240 | 240 | 240 | 240 | 240 | 240 |
| Disodium DL-pyrrolidonecarboxylate | — | 60.0% | 40.0% | 30.0% | 20.0% | 10.0% |
| Sodium hydrogenphosphate | 0.2% | 0.2% | 0.2% | 0.2% | 0.2% | 0.2% |
| Phosphoric acid | q.s. | q.s. | q.s. | q.s. | q.s. | q.s. |
| Sodium hydroxide | q.s. | q.s. | q.s. | q.s. | q.s. | q.s. |
| Sodium chloride | 0.9% | 0.9% | 0.9% | 0.9% | 0.9% | 0.9% |
| Purified water | q.s. | q.s. | q.s. | q.s. | q.s. | q.s. |
| pH | 7.0 | 7.0 | 7.0 | 7.0 | 7.0 | 7.0 |
| Residual rate of enzymatic activity (%), at 30° C. for 7 days | 8.5 | 100.7 | 114.4 | 109.9 | 103.0 | 53.1 |
| Residual rate of enzymatic activity (%), at 30° C. for 14 days | 4.8 | 70.8 | 89.6 | 66.5 | 78.5 | 36.7 |

TABLE 3

| Substance | Formulation B-8 |
|---|---|
| Bioprase | 240 units/ml |
| Sodium lauroylsarcosine[(1)] | 0.5% |
| Triethanolamine lauroyl-L-glutamate[(1)] | 0.5% |
| Sodium stearate[(1)] | 0.25% |
| Polysorbate 80[(2)] | 0.5% |
| Sodium DL-pyrrolidonecarboxylate | 5.0% |
| Disodium hydrogenphosphate | 0.2% |
| Phosphoric acid | q.s. |
| Sodium hydroxide | q.s. |
| Sodium chloride | 0.9% |
| Purified water | q.s. |
| pH | 7.0 |
| Residual rate of enzymatic activity (%), after storage for 14 days at 30° C. | 85.6 |

Notes:
(1): Anionic surfactant
(2): Nonionic surfactant

We claim:

1. A method for stabilizing a preparation for cleansing contact lenses that contains a proteolytic enzyme, the method comprising including in the preparation an amount effective to stabilize the enzyme of a pyrrolidone compound selected from the group consisting of pyrrolidone and pyrrolidone-carboxylic acid and a salt or ester thereof.

2. The method of claim 1, wherein the pyrrolidone compound is included in the preparation at a concentration of not less than 5 (w/v) %.

3. The method of claim 1, wherein the preparation for cleansing contact lenses is in the form of a liquid or solid and exhibits a pH value in the range of 4 to 8 as such or when dissolved in water.

4. The method of claim 1, wherein the proteolytic enzyme is a protease originated from a microorganism belonging to the genus bacillus or trypsin originated from animals.

5. The method of claim 1, wherein the preparation is provided with at least one selected from the group consisting of nonionic, anionic and amphoteric surfactants.

6. The method of claim 5, wherein the concentration of surfactant in the preparation is in the range of 0.01 to 10 (w/v) %.

7. A method for producing a cleansing preparation for contact lenses, comprising including in the preparation a proteolytic enzyme and an amount effective to stabilize the enzyme of a pyrrolidone compound selected from the group consisting of pyrrolidone and pyrrolidone-carboxylic acid and a salt or ester thereof.

8. The process of claim 7, wherein the pyrrolidone compound is included in the preparation at a concentration of not less than 5 (w/v) %.

9. The process of claim 7, wherein the preparation is provided with at least one selected from the group consisting of nonionic, anionic and amphoteric surfactants.

10. The process of claim 9, wherein the concentration of surfactant in the preparation is in the range of 0.01 to 10 (w/v) %.

11. A cleansing preparation for contact lenses, comprising a proteolytic enzyme and an amount effective to stabilize the enzyme of a pyrrolidone compound selected from the group consisting of pyrrolidone and pyrrolidone-carboxylic acid and a salt or ester thereof.

12. The preparation of claim 11, wherein the pyrrolidone compound is present at a concentration of not less than 5 (w/v) %.

13. The preparation of claim 11, further comprising at least one selected from the group consisting of nonionic, anionic and amphoteric surfactants.

14. The preparation of claim 13, wherein the concentration of the surfactant is in the range of 0.01 to 10 (w/v) %.

* * * * *